United States Patent [19]

Stowell

[11] Patent Number: 4,812,741
[45] Date of Patent: Mar. 14, 1989

[54] BALER-MOUNTED CONTINUOUS MOISTURE MONITORING SYSTEM

[76] Inventor: Dennis E. Stowell, P.O. Box 796, Parowan, Utah 84761

[21] Appl. No.: 13,130

[22] Filed: Feb. 10, 1987

[51] Int. Cl.$^4$ ............................................. G01R 27/02
[52] U.S. Cl. ..................................... 324/65 P; 73/73; 56/DIG. 15
[58] Field of Search ................... 56/DIG. 15, 16.4; 73/73; 324/65 P, 65 R, 61 P

[56] References Cited

U.S. PATENT DOCUMENTS

| | | | |
|---|---|---|---|
| 2,503,416 | 4/1950 | Russell . | |
| 2,650,343 | 8/1953 | Thompson | 324/65 P |
| 2,957,130 | 10/1960 | Dietert | 324/65 P |
| 3,047,801 | 7/1962 | Dietert | 324/65 P |
| 3,188,563 | 6/1965 | Jameson | 324/65 P |
| 3,944,916 | 3/1976 | Tillander | 324/65 P |
| 3,999,134 | 12/1976 | Lorenzen . | |
| 4,170,251 | 10/1979 | Hine . | |
| 4,499,111 | 2/1985 | Oetiker . | |
| 4,547,725 | 10/1985 | Oetiker . | |

Primary Examiner—Reinhard J. Eisenzopf
Assistant Examiner—Jose M. Solis
Attorney, Agent, or Firm—Norman B. Rainer

[57] ABSTRACT

A sensing device and interactive components are provided for the continuous automatic monitoring of the moisture content of hay during its baling with a conventional baling machine. The device is comprised of a cylindrical holding tube having an open forward extremity which is welded to the retaining wall of the compression zone of the baler. An electrode and surrounding electrical insulative material are disposed within the holding tube. The forward extremities of the electrode and insulative material extend through an aperture in the retaining wall to coplanar disposition with the interiorly directed surface of the retaining wall. As the hay slides perpendicularly past the electrode, electrical resistivity is measured and caused to indicate moisture content on a meter located in the driver's compartment of the baler machine.

5 Claims, 2 Drawing Sheets

BALER-MOUNTED CONTINUOUS MOISTURE MONITORING SYSTEM

BACKGROUND OF THE INVENTION

This invention concerns the monitoring of the moisture level of hay, and more particularly relates to a specialized sensing device and associated components for the substantially continuous measurement of the moisture level of hay during the baling process.

The moisture level at which hay is baled is critical to the quality of the finished bale. Hay which is baled at a moisture level which is too low (below approximately 10%) shatters during the baling process, causing the leaves to separate from the stems of the plant and pulverize into a fine powder. Hay which is baled at a moisture level which is too high (above approximately 25%) mildews and deteriorates in the bales, resulting in hay which is undesireable as feed. Hay baled at a moisture level above 25% is also susceptible to spontaneous combustion. Hay baled in the 22-25% moisture range tends to turn brown, and is of diminished value as an animal feed.

Various methods of detecting the correct moisture level of hay are available. One method of determining moisture level involves sampling the hay, weighing the sample, drying the sample, weighing the dry sample, and calculating from the two weights the actual moisture level of the sample. This method suffers the disadvantage of being too cumbersome to be practical during the baling operation. In addition, since hundreds of acres of hay may be baled in a single baling session, it is very difficult if not impossible to obtain a representative sample of the hay which is to be baled.

Techniques for measuring the moisture content of hay based upon the direct relationship of electrical conductivity to moisture content are well known. In some such techniques, a sample of hay is placed in the test compartment of an instrument which measures electrical conductivity. In other variations, an elongated probe having two electrodes in its tip is caused to penetrate a bale to provide conductivity readings of interior regions of the bale.

Like the drying and weighing method, earlier conductivity-measuring techniques have the shortcoming of being a batchwise test. Since thousands of bales may be made in one baling session, it is nearly impossible to secure by batchwise test methods truly representative sampling and evaluation of all the hay passing through the baler.

Conventional hay baler machines are generally comprised of: (a) a driver's compartment, (b) a feeder mechanism which picks the hay up from the ground, (c) a section which distributes the hay to form a relatively uniform stream, (d) a forming chamber wherein the stream is compacted to a desired density, producing a tied bundle, and (e) a squeeze rail region where the bundle is further compacted to form the finished bale which is discharged onto the ground. The forming chamber and squeeze rail region, which may be generically characterized as compression zones, have flat retaining walls against which the hay slides as it advances through the baler. The hay will generally pass through said compression zones at a linear flow velocity of between about 150 and 500 inches per minute. The flow is substantially continuous, although having in certain instances a uniformly pulsed motion caused by the compacting mechanisms.

It is accordingly an object of this invention to provide a sensing device as a component of a moisture monitoring system which is continuous in nature and which is directly associated with the baler such that every bale which is baled may be checked for moisture content.

It is a further object of this invention to provide a method utilizing a system as in the foregoing object which determines moisture level of hay during the baling process so that the bailing process can be halted when the moisture content of the hay is outside acceptable limits.

It is a still further object of the present invention to provide a system of the aforesaid nature comprised of apparatus components of rugged, durable construction capable of withstanding the corrosive, abrasive conditions prevalent within a hay baler.

It is yet another object of the invention to provide apparatus of the aforesaid nature amenable to low cost manufacture and facile installation into conventional hay baling equipment.

These objects and other objects and advantages of the invention will be apparent from the following description.

SUMMARY OF THE INVENTION

The above and other beneficial objects and advantages are accomplished in accordance with the present invention by a moisture sensing device for use in a system which continuously monitors the moisture content of hay passing through a conventional baling machine having a driver's compartment and a compression zone having flat retaining walls, said device comprising:

(a) a circular cylindrical steel holding tube having open forward and rearward extremities, (b) an elongated electrode fabricated of a wear resistant electrically conductive solid axially disposed within said holding tube and extending the length thereof, said electrode having forward and rearward extremities, and (c) moisture resistant solid electrical insulator material disposed to fill the annular space between the electrode and the inside wall of said holding tube, (d) the forward extremity of said holding tube being configured to be welded to the exterior surface of the retaining wall about the perimeter of a circular aperture therein, whereby (e) when said holding tube is thereby attached to the exterior surface of the retaining wall, the forward extremity of the electrode and electrical insulator material is substantially coplanar with the interior surface of said retaining wall.

In preferred embodiments, the electrode is a stainless steel bolt, the head of which is oriented to constitute the forward extremity of the electrode. The electrical insulator material may be a machined insert or may be molded in place within the holding tube. In certain embodiments, the insulator material may be slideable within the holding tube. The term "moisture resistant" is intended to denote materials that do not permit diffusion of moisture, and whose maximum moisture holding content is sufficiently low so as not to affect the electrical conductivity of the material. Suitable materials will generally have an equilibrium moisture content on exposure to air at 75 degrees F. and 70% relative humidity of below 3% and preferably below 1%, typical materials being non-porous forms of teflon, phenolic resins such as micarta, and polyester and polyolefin plastics.

A further aspect of the present invention contemplates a system for the continuous monitoring of moisture content of hay during the baling operation, said system comprising:

(a) the afore-mentioned sensing device installed upon a retaining wall of the compression zone, (b) a battery-operated conductivity meter located in the driver's compartment, said conductivity meter having positive and negative input terminals and providing a direct readout of percent moisture, and (c) two electrical conductor wires extending between the sensing device and the input terminals of the conductivity meter, the conductor wire attached to the positive terminal communicating with the rearward extremity of the electrode, and the conductor wire attached to the negative terminal being grounded to the baler.

A still further aspect of this invention contemplates a method for the continuous monitoring of moisture content of hay during the baling operation, said method comprising:

(a) advancing hay in the compression zone of the baler in perpendicular sliding contact across the forward extremity of a sensing device flush mounted with the interior surface of a retaining wall of the compression zone, said sensing device having an electrode surrounded by electrical insulator material, (b) feeding a constant battery voltage in a circuit between the electrode and the metal structure of the baler, said electrode being positive, and said metal structure being a negative ground, (c) continuously measuring the change in electrical resistivity of said circuit, and (d) causing said measured resistivity to be displayed as percent moisture in the driver's compartment.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

For convenience in description, the terms "inner" and "exterior" and equivalents thereto will have reference to the geometric center of the sensing device or compression zone.

DESCRIPTION OF THE PREFERRED EMBODIMENT

Figure 2:
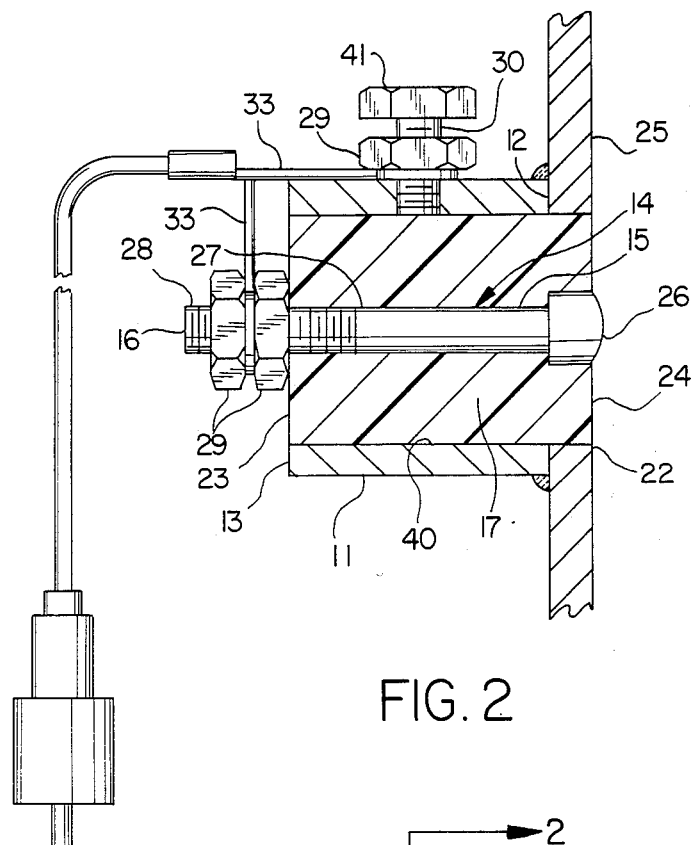
FIG. 2 is a vertical sectional view of the sensing device mounted upon a retaining wall of the compression zone of the baler.
Figure 3:
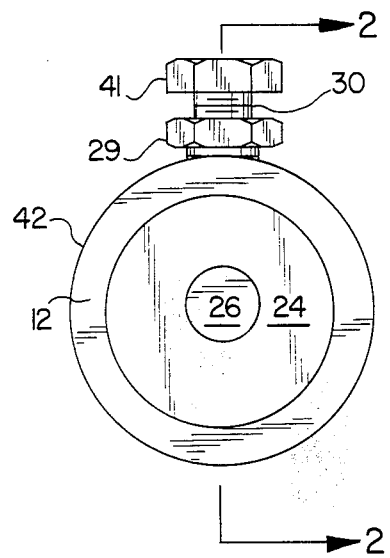
FIG. 3 is an end view of the sensing device viewed from its forward extremity.

Referring to FIGS. 2 and 3, an embodiment of the sensing device 10 of the present invention is shown comprised of circular cylindrical holding tube 11 having open forward and rearward extremities 12 and 13, respectively; elongated electrode 14 disposed within said holding tube in coaxial alignment therewith and extending the length thereof between forward and rearward ends 15 and 16, respectively; and a plug 17 of electrically insulative material machined so as to accommodate electrode 14 and make tight-fitting sliding contact with the inside surface 40 of holding tube 11. Plug 17 has a rearward extremity 23 and a flat forward face 24 perpendicularly disposed to the axis of the holding tube.

The holding tube is fabricated of steel, both extremities of which are cut perpendicularly to the cylindrical axis of the tube. The holding tube may typically have a wall thickness of about ¼", a length of between 1 and 4 inches, and an inside diameter of between 1 and 3 inches.

Figure 1:
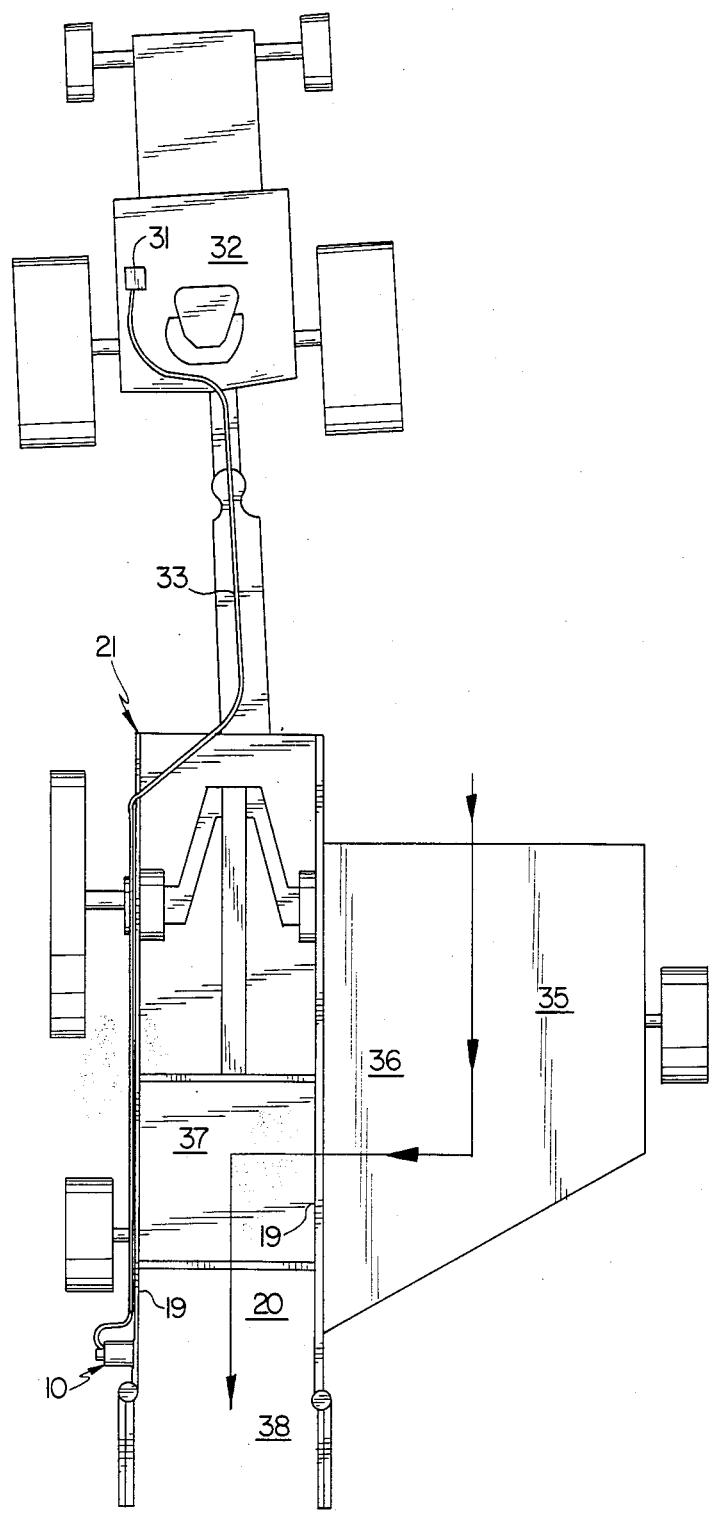
FIG. 1 is a top elevational view of an embodiment of the monitoring system of this invention showing a baler/tractor combination and the relative locations of the three components of the monitoring system, namely the sensing device, the conductivity meter, and the interconnecting electrical conductors.

As shown in FIGS. 1 and 2, the sensing device is installed into operative position by welding forward extremity 12 of the tube to flat vertical retaining wall 19 of the compression zone 20 of baler 21. The welding is done about circular aperture 22 cut through wall 19 and having a diameter which matches the outside diameter of the holding tube. Following the welded attachment of the holding tube to the retaining wall, insulative plug 17 is pushed forwardly so that its forward face 24 is coplanar with the interior surface 25 of retaining wall 19.

The electrode in the exemplified embodiment is a stainless steel bolt, whose forward end has a head 26 of circular diameter greater than the diameter of the shaft portion 27 of the electrode, and adapted to lie in substantially coplanar abutment with the forward face 24 of plug 17. The rearward extremity of the exemplified electrode has a threaded portion 28, which accommodates two nuts 29 capable of gripping an electrical conductor wire.

Bolt 30, having hexagonal head 41, threadably engages the wall of holding tube 11 in perpendicular disposition thereto. Nut 29, engaged by said bolt, is adapted to interact with the outside surface 42 of the holding tube to grip a conductor wire therebetween. Bolt 30 also serves to hold the insulative plug in position.

A battery-operated conductivity meter 31 is mounted within the driver's compartment 32 of the baler machine. The read-out scale of the meter displays percent moisture. The conductivity meter is of substantially conventional design, utilizing a wheatstone bridge circuit to measure electrical resistance. Suitable particular conductivity meters are models DHM-1 and F-4, made by the Delmhorst Instrument Company of Towaco, N.J. Such conductivity meters utilize 9 volt batteries and provide a read out in the form of either a digital display or pivoted indicator needle superimposed above a fixed scale. Lighting means are utilized where necessary to facilitate reading of the meter at night. The meter preferably has calibration means to make suitable adjustments for factors such as ambient temperature, degree of compaction of the hay, and electrode geometry, thereby causing readings to correspond to values producible by the weighing and drying method of analysis.

Paired electrical conductor wires 33 disposed in coaxial format extend between sensing device 10 and conductivity meter 31. The wires preferably have an electrical resistance less than 60 ohm per foot of length so that the total resistivity of the conductor wires is not more than the electrical resistivity produced by sensing device 10. At the sensing device, the conductor wire of negative polarity is connected to post 30 of holding tube 11 or to any part of the baler machine in electrical communication therewith, and the conductor wire of positive polarity is connected to threaded portion 28 of electrode 14.

In operation, hay is drawn into the feeder mechanism 35 of baler machine 21, advanced to distributor section 36, then compacted within a compression zone represented by forming chamber 37 bounded by retaining walls 19, and finally compacted further in squeeze rail section 38 and discharged onto the ground in bale form. As the hay advances through forming chamber 37, it slides perpendicularly across the forward extremity of sensing device 10, and thereby provides a continuous read-out in the driver's compartment of the moisture content of the hay.

The sensing device 10 may also be operatively mounted into the retaining wall of a baler apparatus that rolls the hay into round bales. In such application, the forward extremity is still substantially flush mounted with the interior of the retaining wall, and the hay slides perpendicularly past said forward extremity.

In alternative embodiments, sensing device 10 may be mounted to a spring loaded arm which holds the forward extremity of the device against hay which slides perpendicularly past said extremity.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. A moisture sensing device for use in a system which continuously monitors the moisture content of hay passing through a conventional baling machine having a compression zone having flat retaining walls, said device comprising:
   (a) a circular cylindrical steel holding tube having open forward and rearward extremities, said forward extremity being of circular configuration disposed in a plane perpendicular to the cylinder axis,
   (b) an elongated electrode fabricated of a wear resistant electrically conductive solid axially disposed within said holding tube and extending the length thereof, said electrode having a forward extremity and a rearward extremity adapted to secure an electrical lead wire,
   (c) moisture resistant solid electrical insulator material disposed to fill the annular space between the electrode and the inside wall of said holding tube and between said extremities of the holding tube, said insulator being slideable within said holding tube, and thereby capable of extending forwardly of the forward extremity of said holding tube,
   (d) the forward extremity of said holding tube being configured to be welded to the exterior surface of the retaining wall about the perimeter of a circular aperture therein, whereby
   (e) when said holding tube is thereby attached to the exterior surface of the retaining wall, the forward extremities of the electrode and electrical insulator material are substantially coplanar with the interior surface of said retaining wall.

2. The sensing device of claim 1 wherein the electrode is fabricated of stainless steel.

3. The sensing device of claim 1 wherein said insulator material has an equilibrium moisture content below 3%.

4. A method for the continuous monitoring of moisture content of hay passing through a conventional baling machine having a driver's compartment and a compression zone having flat retaining walls, said method comprising:
   (a) advancing hay in the compression zone of the baler in perpendicular sliding contact across the forward extremity of a sensing device flush mounted with the interior surface of a retaining wall of the compression zone, said sensing device having an electrode surrounded by electrical insulator material,
   (b) feeding a constant battery voltage in a circuit between the electrode and the metal structure of the baler, said electrode being positive, and said metal structure being a negative ground,
   (c) continuously measuring the change in electrical resistivity of said circuit, and
   (d) causing said measured resistivity to be displayed as percent moisture in the driver's compartment.

5. A system for the continuous monitoring of moisture content of hay passing through a conventional baling machine having a driver's compartment and a compression zone having flat retaining walls, said system comprising:
   (a) the sensing device of claim 1 installed upon a retaining wall of the compression zone to place its forward extremity in contact with hay sliding perpendicularly thereby,
   (b) a battery-operated conductivity meter located in the driver's compartment, said conductivity meter having positive and negative input terminals and providing a direct readout of percent moisture, and
   (c) two electrical conductor wires extending between the sensing device and the input terminals of the conductivity meter, the conductor wire attached to the positive terminal communicating with the rearward extremity of the electrode, and the conductor wire attached to the negative terminal being grounded to the baler.

* * * * *